United States Patent [19]

De Rooij et al.

[11] 4,062,927
[45] Dec. 13, 1977

[54] PROCESS FOR THE PREPARATION OF A HYDROXYLAMINE SALT

[75] Inventors: Abraham H. De Rooij; Jozef M. G. Prop; Willem J. Wassen, all of Geleen, Netherlands

[73] Assignee: Stamicarbon, B.V., Geleen, Netherlands

[21] Appl. No.: 695,552

[22] Filed: June 14, 1976

[30] Foreign Application Priority Data

June 16, 1975 Netherlands .......................... 7507119

[51] Int. Cl.$^2$ ............................................. C01B 21/14
[52] U.S. Cl. ..................................... 423/387; 423/56; 423/58; 423/306
[58] Field of Search ..................... 423/56, 58, 306, 61, 423/302, 387, 388

[56] References Cited

U.S. PATENT DOCUMENTS

| 3,758,665 | 9/1973 | Vojkovic | 423/58 |
| 3,767,758 | 10/1973 | Mals et al. | 423/302 |

*Primary Examiner*—Earl C. Thomas
*Attorney, Agent, or Firm*—Cushman, Darby & Cushman

[57] ABSTRACT

An improved process for preparing a hydroxyl-amine salt by reduction of a solution of nitrate ions or nitrogen monoxide. Dissolved molybdenum in amounts as low as about two milligrams per liter of nitrate/nitrogen monoxide solution are known to interfere with the reduction reaction. The present invention provides a simple method of reducing molybdenum contamination, and hence enhancing the efficiency of the reduction reaction. Dissolved molybdenum is removed from the nitrate/nitrogen monoxide solution by coprecipitation with a complex iron-ammonium phosphate. If chromium is present, it will also be removed by this coprecipitation.

8 Claims, No Drawings

PROCESS FOR THE PREPARATION OF A HYDROXYLAMINE SALT

BACKGROUND OF THE INVENTION

The invention relates to an improved process for preparing a hydroxyl-amine salt. Hydroxyl-amine salts may be prepared by reducing nitrate ions or nitrogen monoxide with hydrogen in the presence of a noble metal catalyst in an acidic medium. The resulting hydroxyl-amine salt may be removed from the reaction mixture. The residual reaction mixture, after removal of the hydroxyl-amine salt, may then be reused.

Hydroxyl-amine salts formed by this reaction may be converted into the corresponding oxime by reacting the hydroxyl-amine salt with cycloalkanone to yield the corresponding oxime. Reactions of this type have been described in the U.S. Pat. Nos. 3,641,150; 3,655,760 and 3,701,809, each of which is hereby incorporated by reference. Hydroxyl-amine salts prepared by the improved method of the present invention are thus useful in the preparation of the corresponding oximes. In turn, these corresponding oximes may be used to prepare nylon 6. Other uses of hydroxyl-amine salts prepared by the improved method of the present invention are reducing agent in photography and antioxidant for fatty acids and soaps.

U.S. Pat. No. 3,767,758 and the publication "Nitrogen" 50, pages 27–30 (1967), suggest that in the preparation of a hydroxyl-amine salt by reduction of nitrate ions or nitrogen monoxide, the selectivity of the reaction is adversely affected by the presence of molybdenum in the reaction mixture. The "selectivity" of the reaction is defined as the yield of hydroxyl-amine salt expressed as percentage of the theoretically possible yield.

The apparatus commonly used in the preparation of hydroxyl-amine salts by reduction of nitrate ions or nitrogen monoxide often is constructed of material containing molybdenum. Corrosion of the apparatus and recirculation of the nitrate/nitrogen monoxide reaction mixture may result in molybdenum contamination of the nitrate/nitrogen monoxide reaction mixture. It has been found that an amount of no more than a few milligrams of molybdenum per liter of nitrate/nitrogen monoxide reaction mixture can adversely affect the selectivity of the reduction reaction. It has been found that the selectivity of the reduction of nitrate ions or nitrogen monoxide can be reduced by the presence of molybdenum contamination by as much as 5 to 15%. The use of apparatus constructed from molybdenum-free materials, to avoid molybdenum contamination of the nitrate/nitrogen monoxide reaction mixture, appears to be very expensive. Heretofore, there has been no economical method of reducing molybdenum contamination in the reduction of nitrate ions or nitrogen monoxide to produce a hydroxyl-amine salt.

SUMMARY OF THE INVENTION

The present invention provides an economical process of preparing a hydroxyl-amine salt in a reaction mixture in which molybdenum contamination has been reduced to an acceptable level in a simple manner.

It is an object of the present invention to provide an improved method for preparing hydroxyl-amine salts by reducing nitrate ions or nitrogen monoxide with hydrogen in the presence of a noble metal catalyst in a reaction mixture containing acid.

Another object of the present invention is to provide a simple method of reducing molybdenum contamination to an acceptable level in a reduction reaction of nitrate ions or nitrogen monoxide, thereby improving the selectivity of the reaction. As explained above, the term "selectivity" of the reaction is defined as the yield of hydroxyl-amine salt expressed as percentage of the theoretically possible yield.

A further object of the present invention is to provide a simple method of removing any chromium which may be present in the nitrate/nitrogen monoxide reaction mixture.

Briefly stated, the process of the present invention is an improved method for preparing a hydroxyl-amine salt by reduction of nitrate ions or nitrogen monoxide with hydrogen in the presence of a noble metal catalyst in an acidic reaction medium. The hydroxyl-amine salt produced by the reduction of nitrate ions or nitrogen monoxide may be separated from the acidic reaction mixture and the nitrate/nitrogen monoxide reaction mixture can then be reused. In brief, the improvement of the present invention is a method of removing molybdenum contamination from the nitrate/nitrogen monoxide mixture by coprecipitation of any molybdenum contaminant together with a complex iron-ammonium phosphate precipitate. This coprecipitate of molybdenum and a complex iron-ammonium phosphate can be removed from the reaction mixture, which can then be more efficiently reduced to produce a greater yield of hydroxyl-amine salts. The coprecipitation of contaminating molybdenum together with an iron-ammonium phosphate requires a pH of over about 3.5 and preferably takes place in the presence of less than about 0.2 mole of hydroxyl-amine per kilogram of reaction mixture.

Surprisingly, it has been found that the complex iron-ammonium phosphate precipitate used in the improved process of the present invention also removes contaminating chromium from the reduction reaction mixture.

DETAILED DESCRIPTION OF THE INVENTION

Adequate removal of molybdenum in accordance with the present invention requires the formation of about 10 to about 5,000 grams of the complex iron-ammonium phosphate precipitate per gram of molybdenum to be removed. Preferably the amount of complex iron-ammonium phosphate precipitate formed is between about 150 to about 450 grams per gram of molybdenum to be removed. In the practice of the invention, it has been found that the reaction mixture from which the molybdenum is to be removed must be stirred with the components which form the complex iron-ammonium phosphate precipitate for a certain minimum required time, between about 15 minutes to about 1 hour, in order to insure adequate coprecipitation of the molybdenum together with the complex iron-ammonium phosphate.

The ratio between the components in the complex iron-ammonium phosphate precipitate may vary slightly. The complex iron-ammonium phosphate precipitate normally contains about 0.9 to about 1.1 moles of iron, about 0.3 to about 0.7 moles of ammonium, and about 1 mole of water of hydration per mole of phosphate. A formula for the complex iron-ammonium phosphate precipitate may be:

$$NH_4H[Fe_2(OH)_2(PO_4)_2] \cdot 2H_2O$$

The formation of this complex iron-ammonium phosphate precipitate, of course, requires the presence of iron in the reaction solution. In most cases, it is found that the reduction reaction solution does not contain enough iron to form the required complex iron-ammonium phosphate precipitate. For this reason, additional iron must be added to the reduction reaction solution. Preferably, an iron compound is added which does not contain any anions which are not already present in the reduction reaction solution. Examples of suitable iron compound are the nitrate, phosphate, oxide and hydroxide of divalent and trivalent iron. The concentration of iron in the nitrate/nitrogen monoxide reaction solution should be between about 50 to about 5,000 parts by weight of iron per million parts of the nitrate/nitrogen monoxide reaction solution. Although it is possible to have a higher concentration of iron in the nitrate/nitrogen monoxide reaction solution, this is not found to enhance the removal of molybdenum from the reaction solution. It has been found that the preferred concentration of iron in the nitrate/nitrogen monoxide reaction solution is between about 100 to about 800 parts by weight of iron per million parts of the reduction reaction solution.

Sufficient phosphate must also be present in the nitrate/nitrogen monoxide reaction solution to insure adequate formation of the complex iron-ammonium phosphate precipitate. If the hydroxyl-amine salt to be prepared is an hydroxyl-amine phosphate, sufficient phosphate is usually present in the nitrate/nitrogen monoxide reaction solution for the formation of an adequate amount of the complex iron-ammonium phosphate precipitate to insure thorough removal of molybdenum. Additional phosphate must be added to the nitrate/nitrogen monoxide reaction solution, however, if the hydroxyl-amine salt to be formed is not a hydroxyl-amine phosphate. When additional phosphate is added to the nitrate/nitrogen monoxide reaction solution, it is preferred to add either phosphoric acid or an ammonium phosphate in order to prevent the introduction of any cations not yet present in the reaction solution. In order to insure adequate formation of the required complex iron-ammonium phosphate precipitate the concentration of phosphate in the reduction reaction solution must be between about 1 to about 1,000 millimoles of phosphate per liter of the nitrate/nitrogen monoxide reaction solution for each milligram of molybdenum to be removed. It has been found that molybdenum is present in the nitrate/nitrogen monoxide reaction solution in amounts from about 2 to about 6 milligrams of molybdenum per liter of the reduction reaction solution. Therefore, in the ordinary case, the amount of phosphate required will be about from about 2 millimoles to about 6,000 millimoles of phosphate per liter of the reduction reaction solution. Although larger concentrations of phosphate in the reduction reaction solution are possible, they are not required for the efficient coprecipitation of molybdenum with the complex iron-ammonium phosphate.

Finally, sufficient ammonium ions must be present in the reduction reaction solution to insure adequate formation of the complex iron-ammonium phosphate precipitate. Generally, however, it is not necessary to add additional ammonium ions for this purpose since usually an adequate concentration of ammonium ions is found in the reduction reaction solution. Ammonium ions are ordinarily present in the nitrate/nitrogen monoxide reaction solution at least in part due to a secondary reaction in the reduction of nitrate or nitrogen monoxide to hydroxyl amine The pH of the reduction reaction solution must be at least 3.5 to insure adequate formation of the complex iron-ammonium phosphate precipitate. A pH of above 7 may be used, but does not improve the formation of the complete iron-ammonium phosphate precipitate. Therefore, the pH of the reduction reaction solution is preferably maintained between about 3.5 to about 7. The desired pH is preferably adjusted by the addition of ammonia, for example, ammonium hydroxide, since it insures adequate ammonium ions to produce the required complex iron-ammonium phosphate precipitate.

In order to insure adequate formation of the complex iron-ammonium phosphate precipitate the reduction reaction solution should be maintained between about 20° to about 80° C. Preferably the reduction reaction solution is maintained between a temperature of about 50° to about 70° C.

In the practice of the invention, it has been found that contaminating molybdenum is more completely removed if the reduction reaction solution contains less than about 0.2 mole of hydroxyl amine per kilogram of reduction reaction solution when the contaminating molybdenum is coprecipitated with the complex iron-ammonium phosphate. This low concentration of hydroxyl amine cannot generally be achieved by conventional methods, such as converting the hydroxyl amine into the corresponding oxime by means of a cycloalkanone and removing the oxime from the reaction mixture. In the practice of the present invention, however, a simple method of reducing the hydroxyl amine concentration to less than 0.2 mole of hydroxyl amine per kilogram of the reducing reaction solution has been found. Initially, as much hydroxyl amine as possible is removed in the conventional manner described above. Thereafter the reduction reaction solution is treated with nitrous gases (a gas mixture containing NO and $NO_2$, such as is used in the preparation of nitric acid) so that hydroxyl amine remaining in the solution is decomposed. Preferably, this decomposition of hydroxyl amine takes place at elevated temperatures, preferably between about 45° and about 75° C. The nitrous gases used in the reduction reaction are readily available since they are the starting materials for the preparation of the nitrate ions contained in the reaction solution to be reduced. Alternatively, the required mixture of nitrous gases can be prepared by mixing nitrogen monoxide with air. As yet another alternative, nitric acid may be used for the decomposition of hydroxyl amine instead of the mixture of nitrous gases.

The process according to the invention preferably uses a reaction medium that contains less than 0.05 mole of hydroxyl amine per kilogram, since molybdenum then can be removed very thoroughly. This first removal of the hydroxyl amine from the reaction medium to the required low value can be effected in practice at a low cost.

In practice, the process of the invention can be effected in various ways. For instance, the total amount of reaction medium to be reused can periodically be subjected to the treatment according to the invention. It is also possible to treat only a part of the reaction medium to be reused. The treatment as such can be effected both continuously and batchwise.

The invention will be further elucidated in the following examples

EXAMPLE I

In the preparation of cyclohexanone oxime by reaction of cyclohexanone with hydroxyl-amine phosphate, an aqueous solution that remained after removal of the oxime from the reaction mixture was reused for the preparation of hydroxyl-amine. Per kilogram, this solution contained:

188.5 g of $H_3PO$
5.2 g of $(NH_3OH)_3PO_4$
218.4 g of $NH_4NO_3$
23.3 g of $HNO_3$
564.6 g of $H_2O$
4.2 mg of molybdenum
69.2 mg of iron
38.3 mg of chromium
12.5 mg of nickel The first removal of hydroxyl amine was achieved virtually completely from 30 kg of this solution by passing nitrous gases (19.7% by volume of $NO_2$, 25.6% by volume of $NO$, 54.7% by volume of $N_2$) through the solution for 10 minutes at the rate of 12.5 liters (calculated at 0° C. and 760 mm of Hg) per minute at 60° C. and atmospheric pressure.

Next, 525 milliliters of aqueous ferric-nitrate solution (7.5% by weight $Fe(NO_3)_3$) were added and the pH was raised to 5 by addition of 6037 grams of ammonia water (25% $NH_3$ by weight). The mixture obtained was stirred at about 60° C. for one more hour, after which the resulting coprecipitate (36 grams) of molybdenum and a complex iron-ammonium phosphate was filtered off. 97% of the molybdenum originally present in the solution was removed with this coprecipitate.

984 grams of ammonium nitrate, 8442 grams of nitric acid (concentration 65% by weight of $HNO_3$), 8267 grams of phosphoric acid (concentration 85% by weight of $H_3PO_4$) and 10014 grams of demineralized water were added to 34.7 kilograms of the resulting filtrate, which contained only 3% of the amount of molybdenum present in the original solution. The 62.407 kilograms of aqueous solution thus obtained contained, per kilogram:

196 g of $H_3PO_4$
220 g of $NH_4NO_3$
18.9 g of $HNO_3$
565.1 g of $H_2O$
0.08 mg of molybdenum
22.9 mg of iron
2.4 mg of chromium
5.9 mg of nickel For the reduction of the nitrate (nitrate ions of nitric acid and ammonium nitrate) to hydroxyl amine, this solution was fed, at the rate of 480 grams per hour at atmospheric pressure and 25° C., to a stirred gas scrubber, which contained 15 grams of catalyst (8% by weight of palladium and 2% by weight of platinum, on carbon as a carrier) activated by 4 milligrams of germanium dioxide and through which molecular hydrogen was passed at the rate of 100 liters (calculated to 8° C. and 760 mm of Hg) per hour. On an average, 0.49 kilograms of reaction liquid were discharged per hour through the filter candles in the gas scrubber.

The reaction liquid discharged contained, per kilogram:

49 g of $H_3PO_4$
91.7 g of $(NH_3OH)H_2PO_4$
92 g of $NH_4H_2PO_4$
160 g of $NH_4NO_3$
607.3 g of $H_2O$
0.08 mg of molybdenum
22.9 mg of iron
2.4 mg of chromium
5.9 mg of nickel The selectivity of the reduction of the nitrate to hydroxyl amine amounted to 83%.

Comparative Example A 8405 grams of phosphoric acid (85% by weight of $H_3PO_4$), 989 grams of nitric acid (65% by weight of $HNO_3$), and 18686 grams of demineralized water were added to 30 kilograms of aqueous solution obtained in the preparation of cyclohexanone oxime and having the same composition as in Example I, without molybdenum having been removed from this solution. The solution thus obtained contained, per kilogram:

194.1 g of $H_3PO_4$
2.6 g of $(NH_3OH)_3PO_4$
218.4 g of $NH_4NO_3$
20.2 g of $HNO_3$
564.1 g of $H_2O$
1.8 mg of molybdenum
31.7 mg of iron
17.5 mg of chromium
5.8 mg of nickel The nitrate in the solution was reduced to hydroxyl amine in the way described in Example I. However, the solution was fed to the scrubber at a lower average rate, viz. 350 grams per hour, in order to obtain the same hydroxyl-amine concentration in the final product. The reaction liquid discharged contained, per kilogram:

49 g of $H_3PO_4$
91.7 g of $(NH_3OH)H_2PO_4$
92 g of $NH_4H_2PO_4$
160 g of $NH_4NO_3$
607.3 g of $H_2O$
1.8 mg of molybdenum
31.7 mg of iron
17.5 mg of chromium
5.8 mg of nickel The selectivity of the reduction amounted to only 72%.

Comparative Example B

Example I was repeated, but without the said complete removal of hydroxyl amine. Here only 46% of the original amount of molybdenum was discharged with the precipitate, as a result of which the selectivity of the reduction dropped to 78%.

EXAMPLE II

In the preparation of cyclohexanone oxime by reaction of cyclohexanone with hydroxyl-amine phosphate, an aqueous solution that remained after removal of the oxime from the reaction mixture was reused for the preparation of hydroxyl amine. This solution contained, per kilogram:

117.6 g of $H_3PO_4$
13.1 g of $(NH_3OH)H_2PO_4$
120.8 g of $NH_4H_2PO_4$
176 g of $NH_4NO_3$
572.5 g of $H_2O$
5 mg of molybdenum
83 mg of iron
46 mg of chromium
15 mg of nickel The hydroxyl amine still present was first removed virtually completely from 80 kg of this solution by passing nitrous gases (3.9% by volume of $NO_2$, 5.2% volume of NO, 90.9% by volume of $N_2$) through the solution for 20 minutes at the rate of 103.7 liters (calculated at 0° C. and 760 mm of Hg) per minute at 50° C. and 5 atmospheres.

Next, 57.7 grams of $Fe(NO_3)_3$ were added and the pH was raised to 4.5 by addition of 10.7 kg of ammonia water (25% by weight). The mixture obtained was stirred at about 65° C. for 30 more minutes, after which the resulting precipitate, 69 g, was filtered off.

0.56 kg of ammonium nitrate, 28.79 kg of nitric acid (concentration 65% by weight of $HNO_3$), 15.22 kg of phosphoric acid (concentration 85% by weight of $H_3PO_4$), and 24.93 kg of demineralized water were added to 90.5 kg of the resulting filtrate, which contained only 5% of the amount of molybdenum present in the original solution. The 160 kg of aqueous solution thus obtained, per kilogram:

196 g of $H_3PO_4$
216 g of $NH_4NO_3$
18.9 g of $HNO_3$
569.1 g of $H_2O$
0.12 mg of molybdenum
22 mg of iron
3.5 mg of chromium
7.5 mg of nickel For the reduction of the nitrate (nitrate ions of nitric acid and ammonium nitrate) to hydroxyl amine, this solution was fed, at the rate of 10 kg per hour at a pressure of 10 atmospheres and 60° C., to a stirred gas scrubber (effective content 3.3 liters), which contained 20 grams of catalyst (8% by weight of palladium, 2% by weight of platinum on carbon as a carrier) activated by 40 mg of germanium oxide and through which molecular hydrogen was passed at the rate of 2,000 liters (at 0° C. and 760 mm of Hg) per hour. On an average, 10.1 kg of reaction liquid was discharged per hour through the filter candles in the gas scrubber. The reaction liquid discharged contained, per kilogram:

49 g of $H_3PO_4$
91.7 g of $(NH_3OH)H_2PO_4$
92 g of $NH_4H_2PO_4$
160 g of $NH_4NO_3$
607.3 g of $H_2O$
0.12 mg of molybdenum
22 mg of iron
3.5 mg of chromium
7.5 mg of nickel The selectivity of the reduction of the nitrate to hydroxyl amine amounted to 80%.

Comparative Example C 13.12 kg of ammonium nitrate, 13.57 kg of nitric acid (65% by weight of $HNO_3$), 15.22 kg of phosphoric acid (85% by weight of $H_3PO_4$), and 38.09 kg of demineralized water were added to 80 kg of aqueous solution obtained in the preparation of cyclohexanone oxime and having the same composition as in Example II, without molybdenum having been removed from the solution. The solution thus obtained contained, per kilogram:

191.1 g of $H_3PO_4$
6.6 g of $(NH_3OH)H_2PO_4$
212 g of $NH_4NO_3$
22.1 g of $HNO_3$
568.2 g of $H_2O$
2.5 mg of molybdenum
41.5 mg of iron
23 mg of chromium
7.5 mg of nickel The nitrate in the solution was reduced to hydroxyl amine in the way described in Example II. But the solution was passed through the gas scrubber at a lower average rate, viz. 9 kg per hour, in order to obtain the same hydroxyl-amine concentration in the final product. The reaction liquid discharged contained, per kilogram:

49 g of $H_3PO_4$
91.7 g of $(NH_3OH)H_2PO_4$
92 g of $NH_4H_2PO_4$
160 g of $NH_4NO_3$
607.3 g of $H_2O$
2.5 mg of molybdenum
41.5 mg of iron
23 mg of chromium
7.5 mg of nickel The selectivity of the reduction amounted to 77%.

What is claimed is:

1. An improved process for preparing hydroxylamine salts by reduction of nitrate ions or nitrogen monoxide by means of hydrogen in the presence of a noble metal catalyst in an aqueous reaction medium containing from about 2 to about 6 milligrams of molybdenum per liter by forming a complex iron-ammonium phosphate/molybdenum coprecipitate, comprising:
reducing hydroxyl amine concentration in said reaction medium to less than 0.2 mole of hydroxyl amine per kilogram prior to removing said molybdenum,
removing said 2 to 6 milligrams of molybdenum per liter from said reaction medium by adding an effective amount of iron, ammonium and phosphate salts to form a complex iron-ammonium phosphate/molybdenum coprecipitate in said reaction medium, stirring said reaction medium for a period of at least 15 minutes, forming a complex iron-ammonium phosphate/molybdenum coprecipitate in said reaction medium at a pH of over 3.5 and a temperature between 20° and 80° C., separating said complex iron-ammonium phosphate/molybdenum coprecipitate from said reaction medium, reducing nitrate ions or nitrogen monoxide with hydrogen in the presence of a noble metal catalyst in said reaction medium to form a hydroxyl-amine salt, and removing said hydroxyl-amine salt and reusing the residual reaction medium, whereby the selectivity of said reduction of nitrate ions or nitrogen monoxide is enhanced.

2. The process set forth in claim 1, including reducing hydroxyl amine concentration in said reaction medium to less than 0.05 mole of hydroxyl amine per kilogram to removing said molybdenum.

3. The process set forth in claim 1, wherein said hydroxyl-amine concentration is reduced by first treating said reaction medium with a cycloalkanone to form a corresponding oxime, removing said oxime from said reaction medium, and then treating said reaction medium with a gas mixture containing NO and $NO_2$.

4. The process set forth in claim 2, wherein said hydroxyl amine concentration is reduced by first treating said reaction medium with a cycloalkanone to form a corresponding oxime, removing said oxime from said reaction medium, and then treating said reaction medium with a gas mixture containing NO and $NO_2$.

5. The process set forth in claim 1, wherein said reaction medium forming a complex iron-ammonium phosphate precipitate contains dissolved iron in a concentration of about 100 to about 800 parts by weight per million.

6. The process set forth in claim 1, wherein said complex iron-ammonium phosphate precipitate is formed in an amount of about 150 to about 450 grams for each gram of molybdenum to be removed.

7. The process set forth in claim 1, wherein said reaction medium is maintained at a temperature from about 50° to about 70° C.

8. The process set forth in claim 1, wherein said reaction medium is maintained at a pH of over 3.5 by the addition of aqueous ammonia.

* * * * *